United States Patent [19]

Jacobsen et al.

[11] Patent Number: 6,014,919
[45] Date of Patent: Jan. 18, 2000

[54] METHOD AND APPARATUS FOR FORMING CUTS IN CATHETERS, GUIDEWIRES, AND THE LIKE

[75] Inventors: Stephen C. Jacobsen; Clark Davis, both of Salt Lake City, Utah

[73] Assignee: Precision Vascular Systems, Inc., Salt Lake City, Utah

[21] Appl. No.: 08/714,555

[22] Filed: Sep. 16, 1996

[51] Int. Cl.[7] ............................. B26D 5/02; B26D 5/20; B26D 7/02

[52] U.S. Cl. ................ 83/282; 83/886; 83/210; 83/422; 83/466.1; 83/486

[58] Field of Search ............................. 83/209, 210, 240, 83/248, 257, 282, 409, 418, 421, 457, 465, 466.1, 471.2, 471.3, 485, 486, 486.1, 556, 563, 733, 863, 864, 881, 886, 913, 924, 750, 422; 269/254 R, 902; 279/46.1

[56] References Cited

U.S. PATENT DOCUMENTS

| | | | |
|---|---|---|---|
| 1,553,227 | 9/1925 | Feyk et al. | 83/409 |
| 1,866,888 | 7/1932 | Hawley | 83/471.3 |
| 3,686,990 | 8/1972 | Margolien | 83/409 |
| 4,000,672 | 1/1977 | Sitterer et al. | 83/209 X |
| 4,476,754 | 10/1984 | Ducret | 83/210 X |
| 4,545,390 | 10/1985 | Leary . | |
| 4,574,670 | 3/1986 | Johnson | 83/409 |
| 4,781,092 | 11/1988 | Gaiser | 83/282 X |
| 4,884,579 | 12/1989 | Engelson . | |
| 4,922,777 | 5/1990 | Kawabata | 83/409 X |
| 4,955,862 | 9/1990 | Sepetka . | |
| 4,989,608 | 2/1991 | Ratner . | |
| 4,994,069 | 2/1991 | Ritchart et al. . | |
| 5,009,137 | 4/1991 | Dannatt | 83/209 |
| 5,095,925 | 3/1992 | Engleson . | |
| 5,306,252 | 4/1994 | Yutori et al. . | |
| 5,308,435 | 5/1994 | Ruggles et al. | 83/209 X |
| 5,315,906 | 5/1994 | Ferenczi et al. | 83/282 X |
| 5,376,084 | 12/1994 | Bacich et al. . | |
| 5,437,288 | 8/1995 | Schwartz et al. . | |
| 5,438,993 | 8/1995 | Lynch et al. . | |
| 5,439,000 | 8/1995 | Gunderson et al. . | |
| 5,441,483 | 8/1995 | Avitall . | |
| 5,441,489 | 8/1995 | Utsumi et al. . | |
| 5,460,187 | 10/1995 | Daigle et al. . | |
| 5,477,856 | 12/1995 | Lundquist . | |
| 5,520,645 | 5/1996 | Imran et al. . | |

FOREIGN PATENT DOCUMENTS

| | | |
|---|---|---|
| 25 39 191 | 9/1975 | Germany . |
| PCT/US92/07619 | 9/1992 | WIPO . |

*Primary Examiner*—Rinaldi I. Rada
*Assistant Examiner*—Charles Goodman
*Attorney, Agent, or Firm*—Thorpe, North & Western, LLP

[57] ABSTRACT

A catheter, guidewire or other cylindrical object cutting device which includes a base, at least one circular saw blade mounted on a spindle member, and a clamp for manipulating the object to be cut. The at least one circular saw blade is rotatably mounted on the spindle member. The spindle member is free to move vertically and horizontally with respect to the base to thereby control the location, size and depth of the cuts in a cylindrical object disposed adjacent thereto. The clamp is able to hold the object to be cut, as well as rotate it to expose the entire circumference of the object to the saw blade. By releasing the clamp, a pinch roller can advance the object before the clamp is re-engaged to securely hold the object for cutting. Sensors are also provided to enable detection of wear of the saw blade so as to signal needed replacement or adjustment of the saw blade to compensate.

5 Claims, 7 Drawing Sheets

METHOD AND APPARATUS FOR FORMING CUTS IN CATHETERS, GUIDEWIRES, AND THE LIKE

BACKGROUND

1. Field of the Invention

The present invention pertains to making precision cuts in catheters and guidewires. Specifically, a device for holding, advancing, rotating and then cutting a catheter or guidewire is provided which is able to manipulate the catheter or guidewire in two degrees of freedom to enable precision control of the location of the cuts. Various clamping mechanisms are provided for manipulating the catheter or guidewire, as well as mechanisms for wear detection of saw blades used to make the cuts resulting in controlled variation in mechanical properties.

2. State of the Art

Making cuts in catheters and guidewires requires precision in order to ensure reliability because of the medical applications in which they are used. However, it is also important to control costs of production so that costs to the health care industry can be minimized.

The state of the art is typified by such devices as grinding wires, wound coils, and lasers for making the cuts. But these devices often suffer from high cost or imprecise or difficult control mechanisms for properly positioning both the device to make the cut and the cylindrical object to be cut.

What is needed is a method and apparatus for making cuts in catheters and guidewires which allows precise control of characteristics of the cuts. This entails precision holding, advancement and rotation of the generally cylindrical object while at least one saw blade is itself advanced to make the cut and retracted afterward.

OBJECTS AND SUMMARY OF THE INVENTION

It is an object of the present invention to provide a method and apparatus for forming precision cuts in catheters and guidewires.

It is another object to provide a method and apparatus for forming precision cuts in cylindrical objects.

It is yet another object to provide a method and apparatus for forming precision cuts by manipulating a cylindrical object in two degrees of freedom to control the parameters of the cuts.

It is still another object to provide a method and apparatus for holding, advancing and rotating a cylindrical object to be cut.

Still yet another object of the invention is to provide a method and apparatus for increasing throughput of a device which forms cuts in cylindrical objects by providing multiple saw blades on a single cutting tool.

It is another object to provide a method and apparatus for detecting the extent of wear of a saw blade in order to more precisely control the position of the saw blade.

These and other objects of the present invention are realized in a preferred embodiment of a device for making cuts in a catheter, guidewire or other cylindrical object. The device includes a base which has at least one circular saw blade mounted on a spindle member, and a clamp for manipulating and positioning the object to be cut. The circular saw blade is rotatably mounted on the spindle member. The spindle member is free to move vertically and horizontally with respect to the base to thereby control the location, length, depth and angle of the cuts in a cylindrical object disposed adjacent thereto. The clamp is able to hold the object to be cut, as well as position it by, for example, rotation to thereby expose the entire circumference of the cylindrical object to the saw blade. By releasing the clamp, a pinch roller advances the cylindrical object before the clamp is re-engaged to securely hold the cylindrical object for cutting.

Another aspect of the invention is the ability to make precision cuts by providing means for controlling the rotation and advancement of the object to be cut and movement of the saw blade spindle member. Sensors are also provided to enable detection of wear on the saw blade so as to signal needed replacement or adjustment of the location of the saw blade spindle member to compensate.

Another aspect is the ability to simultaneously make a plurality of cuts in the object. This is accomplished with a saw blade having a plurality of blades in parallel. Even more cuts can be made by providing more than one saw blade spindle member, where each is independently movable in two degrees of freedom.

Another aspect of the invention is to provide more than one spindle member so that blades can simultaneously make precision cuts at different locations along the length of the cylindrical object.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1A:
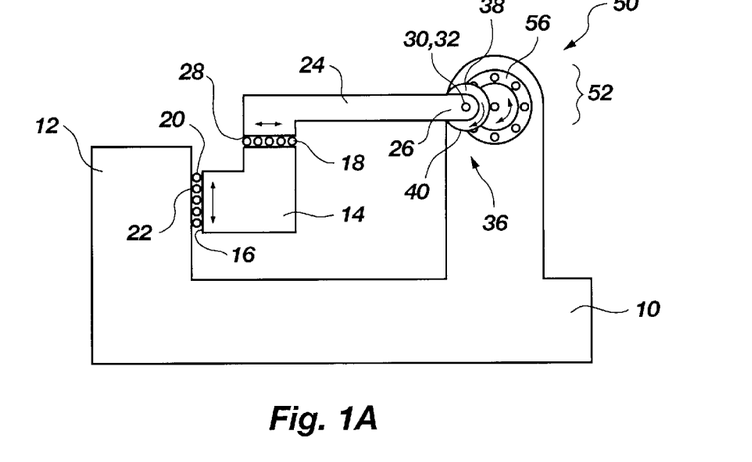
FIG. 1A is a front elevational view of a preferred embodiment made in accordance with the principles of the present invention.
Figure 1B:
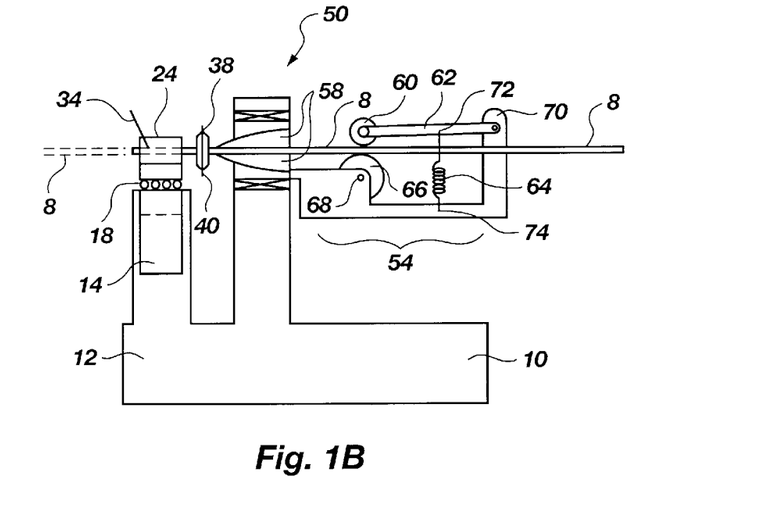
FIG. 1B is a side elevational view of the invention shown in FIG. 1A.

The present invention is illustrated in FIGS. 1A and 1B. FIG. 1A is a front view of the preferred embodiment of the invention, and shows the system for forming precision cuts in a catheter, a guidewire, or other cylindrical objects. For purposes of keeping in mind the intended use of the present invention, a catheter will be referred to as the object being cut, although any cylindrical object can be substituted for the catheter. However, reference to the catheter is only for the convenience of writing in terms of a specific cylindrical object, and should not be considered a material limitation of the invention. However, referring to a catheter keeps present in mind the objective of having a very precise cutting device, where precision is paramount in most medical applications. Furthermore, a catheter is only one embodiment of a medical application, but which easily represents the need for precision.

The system 6 shown in FIGS. 1A and 1B is comprised of several elements including a base member 10 for supporting the structure. Coupled in sliding engagement with a vertical base member 12 is a vertically movable member 14 which has a first vertical coupling face 16 and a first horizontal coupling face 18. The vertical coupling face 16 is slidingly engaged with a base member vertical coupling face 20.

The mechanism 22 for enabling the sliding engagement between the vertical coupling face 16 and the base member vertical coupling face 20 can be any appropriate apparatus. The important consideration is that the vertically movable member 14 not be permitted to move horizontally, or the precision of the system will be compromised. Therefore, the tolerances of the mechanism 22 must necessarily be small. A good example of an appropriate mechanism 22 is well known to those skilled in the art as a crossed roller bearing slide.

Figure 2:
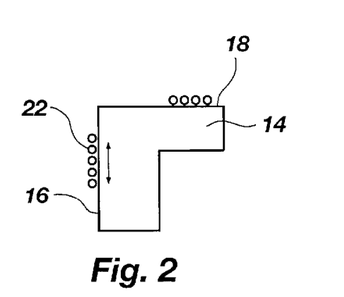
FIG. 2 is an alternative embodiment of a vertically moving member shown reversed in orientation with respect to FIGS. 1A and 1B.
Figure 3:
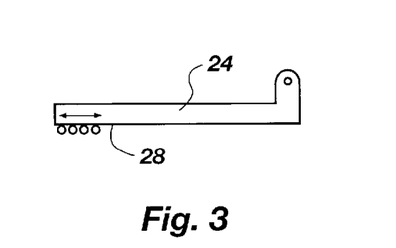
FIG. 3 is an alternative embodiment of a horizontally moving member shown reversed in orientation with respect to FIGS. 1A and 1B.

The shape of the vertically movable member 14 is shown here as a small backwards "L". An alternative shape for the vertically movable member 14 is shown in FIG. 2. The member 14 is flipped over as compared to the embodiment of FIG. 1A. The important feature of the member 14 is that it provide two faces 16, 18 which can be slidably engaged to move vertically and provide a second face on which another member can slidably engage to move horizontally.

The system in FIGS. 1A and 1B is also comprised of a horizontally movable member 24 which has a spindle end 26 and a second horizontal coupling face 28. This horizontally movable member 24 is slidably engaged at its second horizontal coupling face 28 to the vertically movable member 14 at its first horizontal coupling face 18. It should be observed that the vertically movable member 14 and the horizontally movable member 24 are capable of moving independently of each other. In this way, the system achieves two independent degrees of freedom of movement.

The spindle end 26 of the horizontally movable member 24 provides a horizontal slot 30 in which a spindle 32 is disposed. The slot 30 is generally circular to serve as a receptor for the round shaft 34 of the spindle 32. The spindle shaft 34 has disposed on a working end 36 thereof at least one circular saw blade 38. The circular saw blade 38 is disposed vertically on the spindle shaft 34, but may also be angled in other embodiments.

The spindle shaft 34 is coupled to a drive motor by gears, belts, direct drive, or any other appropriate means (not shown) which will cause the spindle shaft 34 to rapidly rotate. The drive motor (not shown) can be disposed in any appropriate location relative to the spindle shaft. In a preferred embodiment, the spindle shaft 34 is driven by a brushless DC motor through a toothed timing belt.

The circular saw blade 38 is typical of those found in the art. In a preferred embodiment, the cutting edge 40 of the saw blade 38 is coated with industrial diamonds.

The means for holding and otherwise manipulating a catheter 8 to be cut is the clamping member 50. The clamping member 50 is comprised of two major assemblies: the clamp 52 and the clamp feeding (supplying) means 54, or the device which feeds the catheter 8 to and then through the clamp 52. The clamping member 50 is also coupled to the base member 10 and disposed to hold the clamp 52 in a position for easy feeding of the catheter 8 to the circular saw blade 38.

In the preferred embodiment, the clamp 52 is of the type known to those skilled in the art as a collet clamp. A collet clamp is a slotted cylindrical clamp inserted tightly into the tapered interior of a sleeve or chuck on a lathe to hold a cylindrical piece of work. In FIG. 1A, the cylindrical shape of the clamp 52 is visible. It is slotted in that the clamping arms 58 are separate from each other so that they can pull away from the catheter 8 when disengaging, and then securely come together around the catheter 8 when engaging.

In a preferred embodiment, a desirable feature of the clamp 52 is that it is rotatably mounted within the clamping member 50. The collet clamp 52 can then rotate so as to dispose a different portion of the surface of the catheter 8 to the saw blades 38. The mechanism for rotating the clamp 52 is shown generally at 56, and is comprised of the clamp 52 which is held in a frame which can rotate with respect to the saw blade 38.

The clamp feeding (supplying) means 54 seen in FIG. 1B is shown in this preferred embodiment to be comprised of a pinch roller assembly which includes a pinch roller 60, a lever arm 62, a spring 64, and a feed roller 66. As FIG. 1B should make clear, the pinch roller assembly 60, 62, 64, 66 feeds the catheter 8 to the clamp 52 by using friction created between two opposing members 60, 66. The upper member is the pinch roller 60. The lower member is the feed roller 66. The feed roller 66 has an axle 68 mounted in the clamp feeding means 54 so that the feed roller 66 can roll. The pinch roller 60 is disposed at the end of a lever arm 62 which pivots at a pivoting end 70. Located distally from the pinch roller assembly along the length of the lever arm is a hole 72.

One end of a spring 64 is inserted therethrough, and the other end of the spring 64 is coupled at another hole 74 to the clamp feeding means 54. The spring 64 provides the tension necessary for the feed roller 64 to push the catheter 8 to the clamp 52.

Having described most of the components in a preferred embodiment of the catheter cutting assembly 6, the operation of the assembly 6 is as follows. First, the uncut catheter 8 is placed between the pinch roller 60 and the feed roller 66. This can be done by raising the lever arm 62 by stretching the spring 64. Releasing the lever arm 62 causes the pinch roller 60 to push down against the feed roller 66, with the catheter 8 disposed therebetween. A drive mechanism (not shown) is coupled to the feed roller 66 to cause it to roll and thereby push the catheter 8 toward the clamp 52. The clamp 52 should be in a disengaged position (hole through clamp is larger than diameter of the catheter 8) so that the catheter 8 can be fed easily therethrough. After passing through the clamp 52, the catheter 8 is fed sufficiently far past the circular saw blade 38 so that it is in a proper position to have an incision made in or through its surface.

When the catheter 8 is positioned correctly, the clamp 52 is engaged and the saw blade 38 is advanced to make cutting contact. Before cutting, the saw blade 38 will always be positioned in a retracted position. The retracted position is both vertically below and horizontally pulled away from the catheter 8. The first movement of the saw blade 38 is 1) horizontal advancement toward the catheter 8. This is accomplished by moving the horizontally movable member 24 relative to the vertically movable member 14 to which it is attached. The horizontally movable member 24 is moved until it has reach the depth of the incision to be made in the catheter 8. The next step 2) comprises the vertically movable member 14 moving upwards relative to the base 10 to which is coupled to thereby make the cut. The saw blade 38 is then immediately retracted by moving the vertically movable member 14 away from the catheter 8. The horizontal member is moved only when the next cut is at a different depth or when all cutting is complete.

If another cut is to be made, the collet clamp 52 is released as step 4). The catheter 8 is then fed through the clamp 52 by the feed roller 66 as step 5). The collet clamp 52 is then reengaged in step 6) and, if necessary, the collet clamp 52 is rotated to expose a different position of the catheter 8 to the saw blade 38. The saw blade 38 is then moved horizontally if the depth of cut is to change, and then vertically to make the cut and steps 1) through 7) repeat as often as necessary until all the incisions have been made or the catheter 8 is no longer capable of being grasped by the feed roller 66 and opposing pinch roller 60.

The above description of the operation of the catheter cutting system 6 describes the different roles served by the clamp 52. When the circular saw blade 38 is making a cut in the catheter 8, the clamp 52 holds the catheter 8 steady. When the cut has been made in the catheter 8, the catheter 8 is fed through the clamp 52 by causing the clamp to disengage from around the catheter 8. After being disengaged, the catheter 8 is fed through the clamp 52 until the next incision point on the catheter 8 is in position relative to the saw blade 38. The clamp 52 re-engages so as to be disposed snugly around the catheter 8 to again prevent movement of the catheter 8 during cutting.

It should be recognized from the description above that the width of a cut into the catheter 8 is limited to the width of the circular saw blade 38. A wider cut therefore requires that the catheter 8 be advanced slightly past the saw blade 38. However, advancement does not take place while making a cut. The saw blade 38 must be withdrawn so that the clamp 52 can disengage from around the catheter 8 while it is advanced. This is necessary because allowing cutting of the catheter 8 when the clamp is disengaged would create a useless if not imprecise cut.

Another vital component of the assembly 6 is a position sensing means. While it is now understood how the catheter 8 is cut, it is not been explained how the feed roller 66 knows when to stop feeding the catheter 8 through the clamp 52, or how far the clamp 52 needs to rotate before cutting commences. In other words, precision cutting also requires precision positioning of the catheter. Precise positioning requires sensors which can detect where the catheter 8 is in relation to the saw blade 38 and the clamp and then provide this information to some control device which coordinates movement of all components by sending the necessary signals to correctly position all of the system 6 components.

Figure 4:
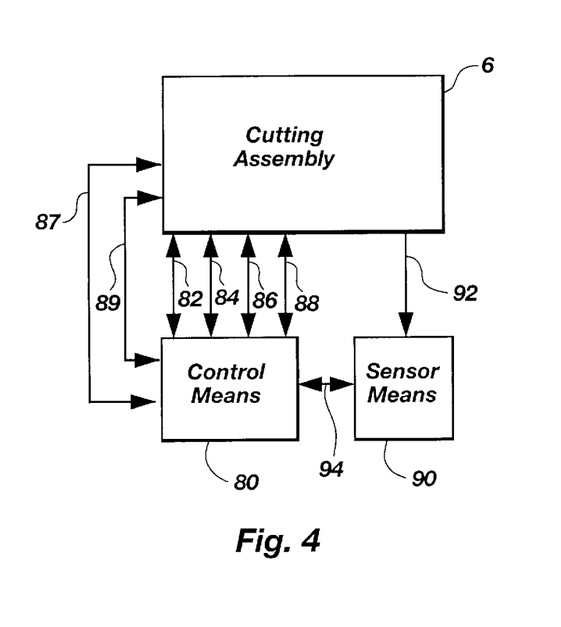
FIG. 4 is a block diagram of the preferred embodiment which shows a control means and sensor means for controlling position determination and movement of components.

This concept is shown generally in the block diagram of FIG. 4. The catheter cutting system 6 is shown as having inputs from a control means 80 for positioning the vertically movable member 14 and shown as arrow 82, the input shown as arrow 84 for positioning the horizontally movable means 24, the arrow 86 which designates an input for controlling rotation of the clamp 52, and an arrow 88 which designates an input for controlling the feed roller 66. Two control inputs for the clamp and the spindle motor are also shown as arrows 87 and 89, respectively. The block diagram in FIG. 4 also shows a sensor means 90 for receiving position information from the system 6 as indicated by arrow 92. This information is transmitted to the control means 80 as indicated by arrow 94 so that it can be processed and the correct control signals 82, 84, 86, and 88 can be transmitted to the system 6.

Figure 5:
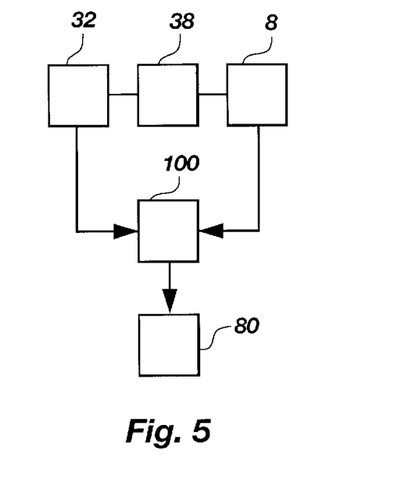
FIG. 5 is a block diagram showing signals which pass between components when using an electrical conduction sensor.

There are several alternative methods for determining the position of the catheter 8 relative to the saw blade 38. These devices can all be substituted as the sensor means 90 of FIG. 4. The first device is an electrical conduction sensing circuit 100 shown in block diagram form as FIG. 5. It is sometimes the case that the materials used in catheters 8 are electrically conductive. Furthermore, the saw blade 38 can also be electrically conductive. Consequently, bringing the saw blade 38 into contact with the conductive catheter 8 can result in the completion of an electrical circuit. By moving the saw blade 38 sufficiently slowly so as not to abruptly make contact with the catheter 8, the moment of contact can be used as a reference point so that the saw blade 38 can be moved the proper horizontal distance to make the desired cut.

Figures 6, 7:
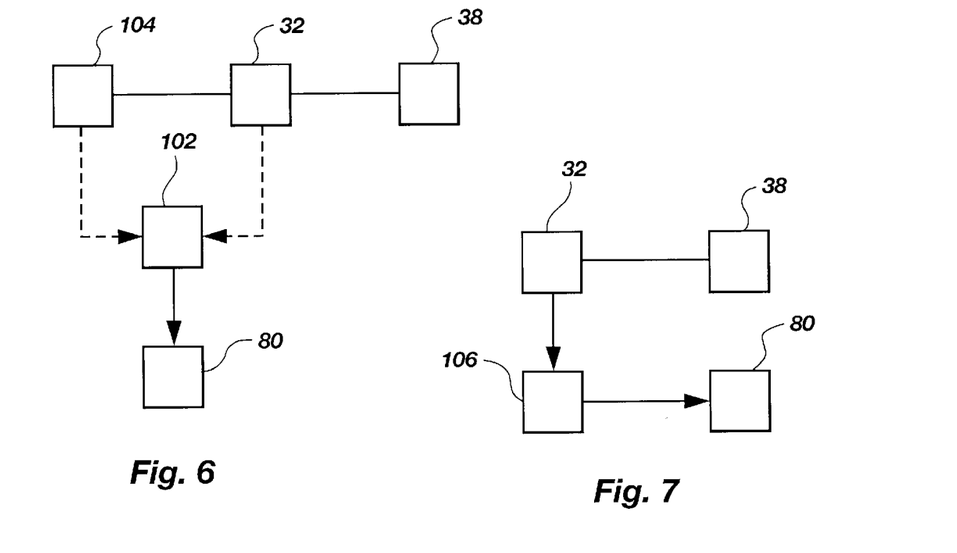
FIG. 6 is a block diagram showing signals which pass between components when using a mechanical drag detection sensor.
FIG. 7 is a block diagram showing signals which pass between components when using a rotation detector sensor.

FIG. 6 shows an alternative method of position sensing. In this embodiment, mechanical drag detection means is coupled to the saw blade 38. The drag detection means 102 can be coupled to either the driving means 104 of the saw blade 38, or the spindle 32 of the saw blade 38. In other words, the drag detection means 102 is any suitable device for detecting when a dragging force is encountered by the saw blade 38. For example, one device for this purpose is a torque transducer which measures the torque loading of the shaft which turns the blade 38.

FIG. 7 shows a related method of position sensing is to use a rotation detector means 106 which detects even slight partial revolutions of the saw blade 38 as the spindle is oscillated vertically and slowly advanced horizontally. With the blade 38 not spinning, rotation of the blade 38 will occur when slight contact is made between the blade with the catheter.

Figure 8:
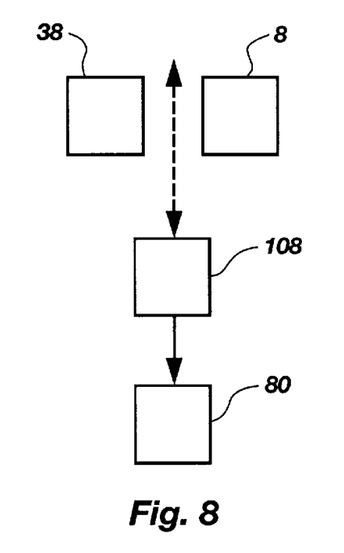
FIG. 8 is a block diagram showing signals which pass between components when using an optical detection sensor.

A final embodiment for detecting the position of the saw blade 38 relative to the catheter 8 is to use an optical detector 108, as shown in block diagram form in FIG. 8. The optical detector means 108 is disposed such that it can detect contact between the saw blade 38 and the catheter 8. There are various optical devices which can be used to implement this detector 108.

One aspect of the invention which is related to the various sensing means 90 described above is that not only is it important to know the position of the blade, but it is also important to know the degree of wear of the blade. All of the sensor embodiments above are inherently able to compensate for the wear which the blade 38 will experience. In other words, none of the methods for determining the exact position of the blade 38 rely on an assumption that the size of the blade 38 is constant. All of the sensor embodiments 90 account for saw blade 38 wear by dynamic determination of position which is not based on a predefined size of the saw blade 38. Instead, the sensors 90 determine when contact is being made, and adjust the position of the blade 38 or the catheter 8 accordingly.

Figure 9A:
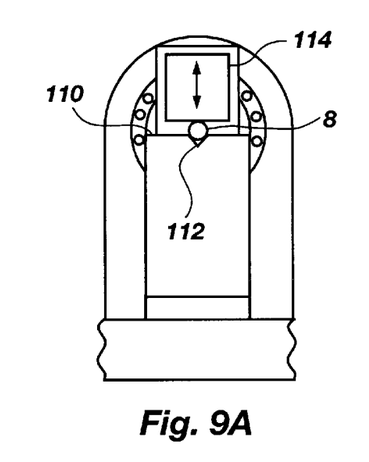
FIG. 9A is a front elevational view of an alternative embodiment for the clamping means.
Figure 9B:
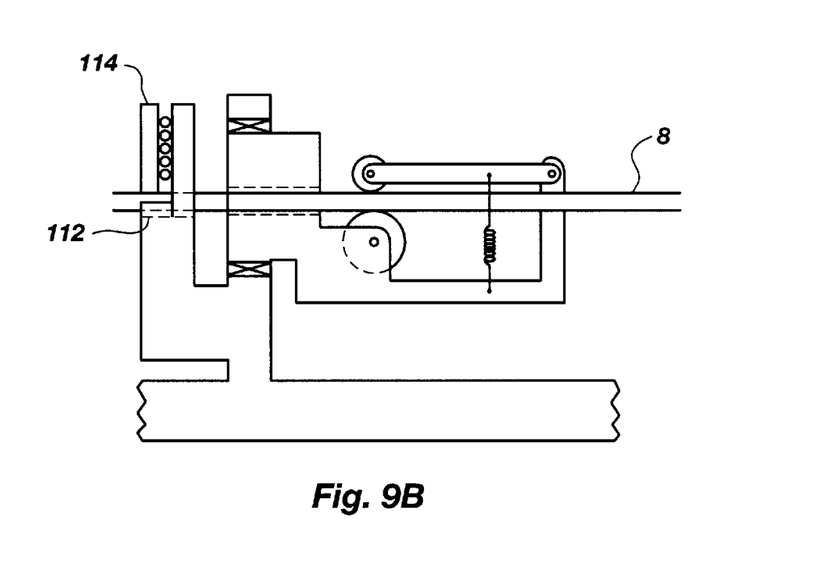
FIG. 9B is a side elevational view of the alternative embodiment for the clamping means of FIG. 9A.

Variations of the preferred embodiment are illustrated in FIGS. 9A and 9B which show that the clamping means 52 has been modified. AS can be seen in FIG. 9A, a stationary support surface 110 is provided with a slot 112 therein for supporting the catheter 8 from below. The slot 112 guides and holds the catheter 8 before, during and after cutting. Holding the catheter 8 not only allows more precise cutting, but prevents damage to the catheter 8 which might otherwise occur. A movable clamping member 114 or anvil is also provided to thereby apply force to the catheter 8 which is clamped between the anvil 114 and the slotted support surface 110. FIG. 9B also shows that the anvil 114 has a mechanism 116 which allows the anvil 114 to move vertically with respect to the support surface 110. In FIG. 9B, the vertical movement mechanism 116 is shown as bearings.

Figure 9C:
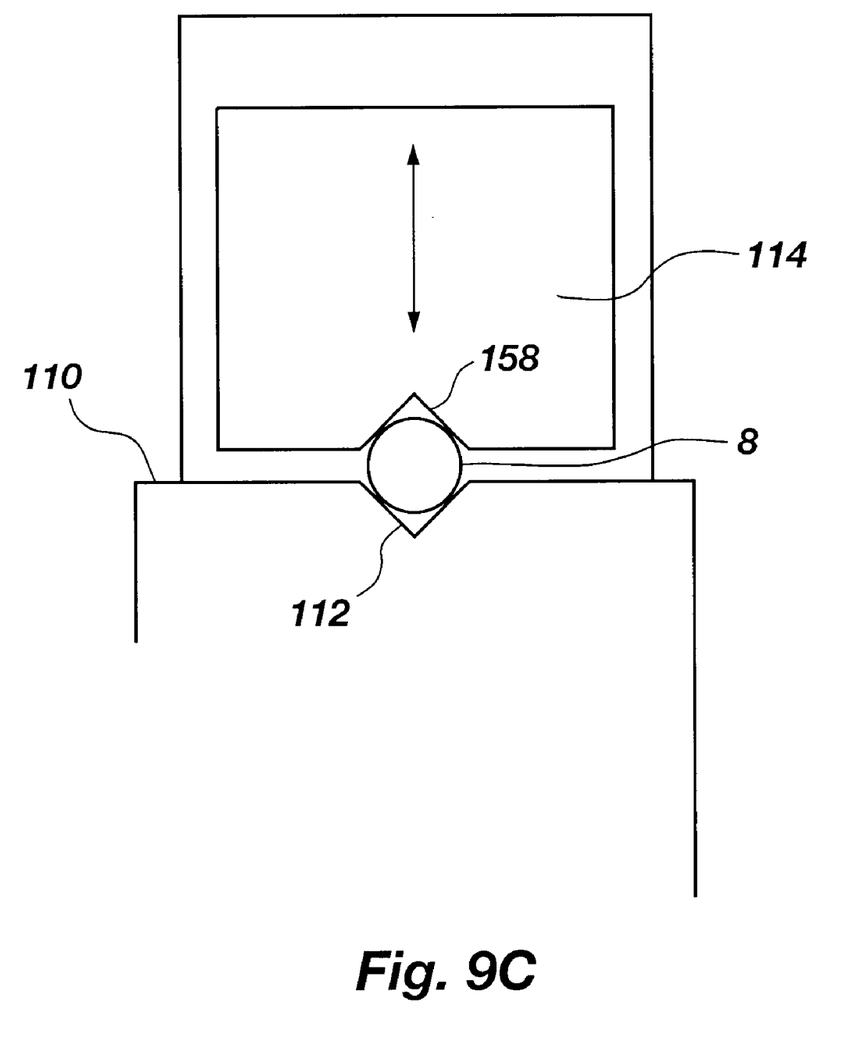
FIG. 9C is a front view which shows that the anvil has a slot.

FIG. 9C is provided to illustrate an alternative embodiment of the anvil 114. As shown, the anvil 114 has a slot 158 which will hold the catheter 8 more securely for cutting.

Figure 10:
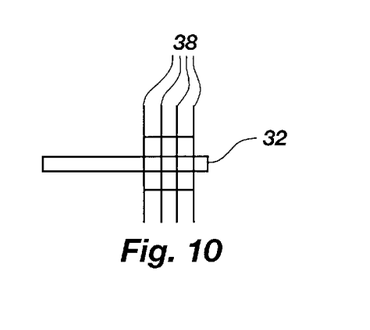
FIG. 10 is an alternative saw blade assembly which can be used in all embodiments of the present invention.

FIG. 10 illustrates a modification to the spindle 32 and saw blade 38 arrangement shown in FIGS. 1A and 1B. Specifically, a plurality of saw blades 38 are shown as being mounted in parallel on the same spindle 32. This also means that the saw blades 38 are necessarily coaxial. It is also preferred that. the saw blades 38 have the same diameter so that no individual saw blade 38 makes a deeper incision in the catheter 8 than any of the others. However, it should be apparent that if the spindle 32 or the saw blades 38 are easily detachable from the system 6, then saw blades of varying diameters might be mounted on the same spindle 32 to achieve a consistent pattern of cuts having different depths.

Figure 11A:
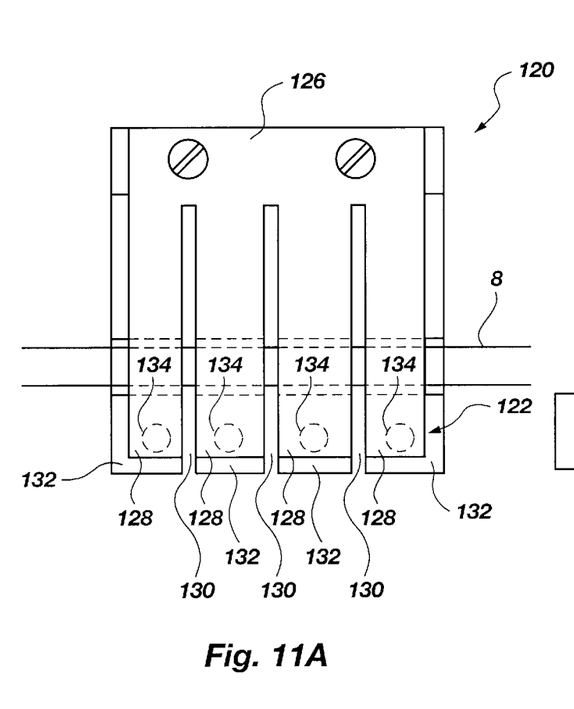
FIG. 11A is a top elevational view of an alternative clamping device.

FIG. 11A shows a clamp mechanism 120 which should be used in conjunction with the multiple saw blade 38 assembly of FIG. 10. The clamp mechanism 120 is capable of holding a catheter 8 in place while the catheter 8 is cut by the plurality of saw blades 38. This is accomplished by providing a clamping surface 122 having a depression or slot 124 for receiving the catheter 8. Coupled to the clamping surface is a leaf spring 126. The leaf spring 126 is comprised of several fingers 128 which force the catheter 8 to remain in the slot 124 while it is cut. Disposed perpendicular to the slot 124 and extending from the clamping surface 122 completely through the clamping mechanism 120 to a back side 136 are a plurality of slots 130 (which make clamp fingers 132) through which the saw blades 38 are extended to thereby cut the catheter 8. The fingers 128 of the leaf spring 126 are typically spaced apart a distance which is equal to the spacing between the plurality of slots 130. This ensures that the saw blades 38 do not inadvertently make contact with the leaf spring fingers 128 while cutting the catheter 8.

To allow the catheter 8 to be fed through the slot 124 in the clamping surface 122, there must be a mechanism for raising the fingers 128 of the leaf spring 126 from off the clamping surface 122. FIG. 11A shows a plurality of holes 134 through the clamping mechanism 120, one hole 134 per clamp finger 132.

Figure 11B:
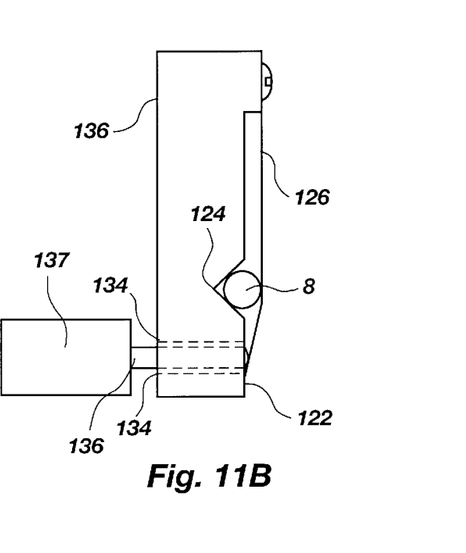
FIG. 11B is a side elevational view of the alternative clamping device of FIG. 11B.

FIG. 11B shows these holes 134, and more importantly, the plurality of push rods 138 which extend through the holes 134 from the back side 136 of the clamp mechanism 120 to the clamping surface 122.

Figure 12:
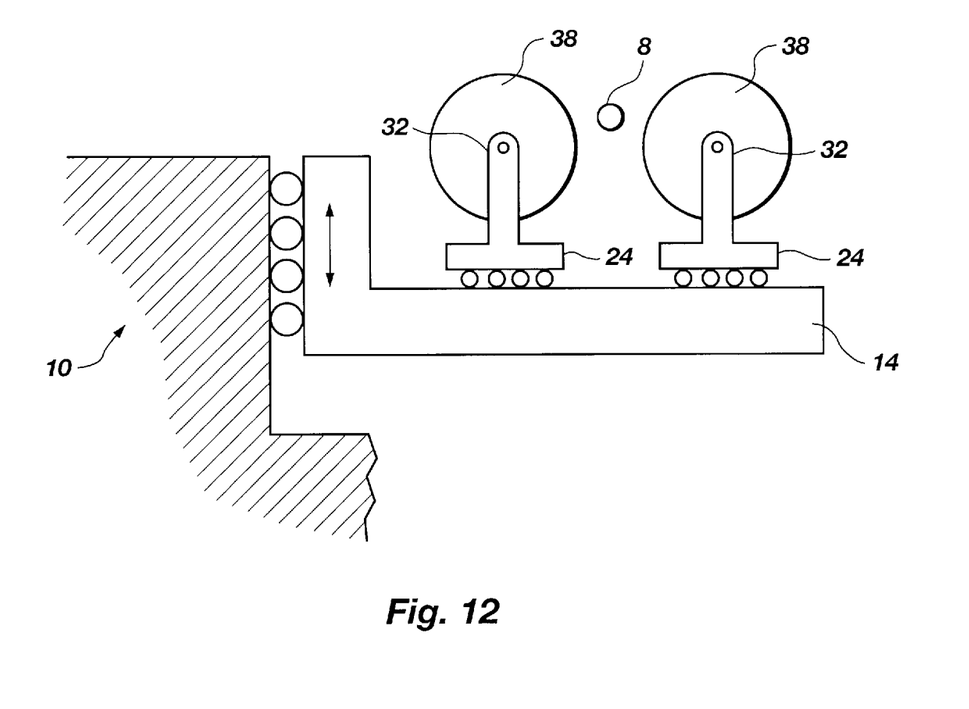
FIG. 12 is an alternative embodiment which uses two saw blade assemblies to simultaneously make incisions in the catheter.

FIG. 12 is an illustration of another alternative embodiment of the present invention. The vertically movable member 14 is shown having another shape which enables it to have disposed thereon two horizontally movable members 24, each having its own associated saw blade or blades 38. This embodiment enables the catheter 8 to be simultaneously cut at different circumferentially defined points on the catheter surface. This is especially useful in making cuts in catheters which having multiple incisions. for example, on diametrically opposed positions on the catheter 8.

Figure 13:
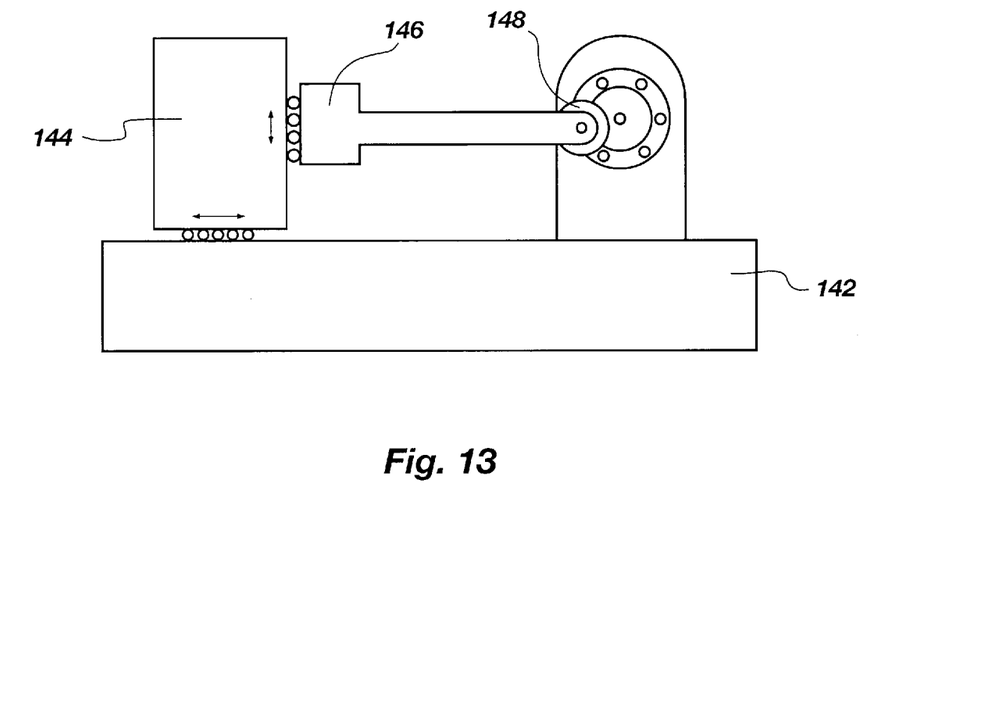
FIG. 13 is a side view of an alternative embodiment which shows a configuration with a base member, a horizontally movable member, and a vertically moveable member.

FIG. 13 is another alternative embodiment of the present invention. It illustrates a horizontally movable member 144 mounted and movable coupled to the base member 142. The vertically movable member 146 is then movable coupled to the horizontally movable member 144, and the cutting instrument 148 is coupled to the vertically movable member 146.

Figure 14:
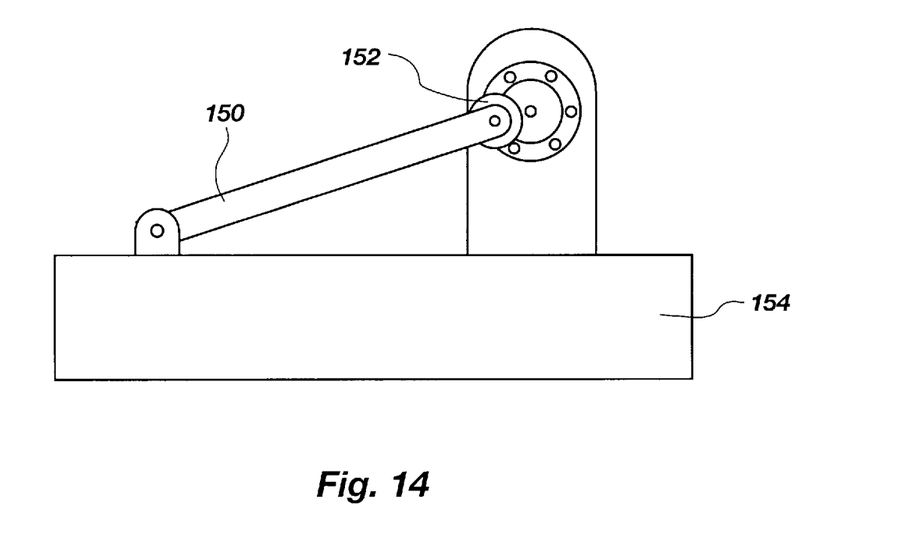
FIG. 14 is another side view of an alternative embodiment which shows a configuration of a base member, and a lever arm which moves the cutting blade in horizontal and vertical directions.

FIG. 14 is another alternative embodiment of the present invention. It illustrates a lever arm 150 coupled to the base member 154, which moves the cutting instrument 152 in a vertical and horizontal manner just by raising and lowering the lever arm 150.

It should be noted that while the preferred embodiment has been defined as having a horizontally movable member with the spindle for the saw blade coupled thereto, the placement of the vertically and horizontally movable members can be switched. In this arrangement, the horizontally movable member is coupled to the base member and the vertically movable member, and the vertically movable member has a spindle rotatably coupled thereto.

An alternative embodiment of the present invention uses a lever arm which is capable of movement in at least two degrees of freedom so that it can move vertically and horizontally to position a spindle end.

Another aspect of the invention which should be clarified is that rotating the catheter is not limited to using a rotatable clamping mechanism. For example, the clamp can be non-rotatable and disengaged to enable the catheter feeding mechanism to rotate the catheter, and then reengage the clamp to make additional incisions. Furthermore, the clamp and the catheter feeding mechanism can be rotated together before additional incisions are made.

It is to be understood that the above-described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A system for forming precision cuts in a catheter, said system comprising:

a base member;

a vertically movable member slidably coupled to the base member;

a horizontally moveable member having a spindle end and being slidably coupled to the vertically movable member;

at least one rotatable spindle disposed through the spindle end;

a plurality of circular saw blades, wherein the saw blades are mounted in parallel and coaxially on the at least one spindle, and wherein each of the plurality of circular saw blades has a same diameter;

a drive means coupled to the at least one spindle for rotating the at least one circular saw blade;

a clamping member coupled to the base member;

a clamping device disposed within the clamping member to thereby engage the catheter while the at least one circular saw blade makes an incision there through; and further comprising:

a clamping surface wherein a depression is disposed there across for partially receiving and holding straight the catheter;

a plurality of slots extending from the clamping surface through to an oppositely facing back side;

a leaf spring coupled to the clamping surface for forcing the catheter into the depression and against the clamping surface;

a plurality of access holes in between the plurality of slots and extending from the back side through to the clamping surface and;

a plurality of push rods, where in each one of the plurality of push rods is disposed within each of the plurality of access holes to thereby lift the leaf spring from off the catheter when the catheter must be manipulated; and means for feeding the catheter to the clamping device.

2. The system as defined in claim 1 wherein the means for feeding the catheter to the clamping device is comprised of a pinch roller assembly disposed adjacent the clamping device to thereby feed the catheter to the clamping device.

3. The system as defined in claim 2 wherein the pinch roller assembly is comprised of:

a first wheel for supporting and forcing the catheter to move to the clamping device when the catheter is disengaged;

a second wheel for applying a force to the catheter to the clamping device; and a lever arm coupled to the base member at a pivoting end, and coupled to the second wheel at a movable end, wherein a spring means coupled between the lever arm and the base member provides the force of the second wheel.

4. The system as defined in claim 1 wherein the system further comprises replacing the catheter with another object to be cut which is selected from the group of objects comprising guide wires and elongate, generally cylindrical objects.

5. A system for forming precision cuts in a catheter, said system comprising:

a base member;

a vertically movable member slidably coupled to the base member;

a horizontally moveable member having a spindle end and being slidably coupled to the vertically movable member;

at least one rotatable spindle disposed through the spindle end;

a plurality of circular saw blades, wherein the saw blades are mounted in parallel and coaxially on the at least one spindle, and wherein each of the plurality of circular saw blades has a same diameter;

a drive means coupled to the at least one spindle for rotating the at least one circular saw blade;

a clamping member coupled to the base member;

a clamping device disposed within the clamping member to thereby engage the catheter while the at least one circular saw blade makes an incision there through; further comprised of:

a clamping surface wherein a depression is disposed there across for partially receiving and holding straight the catheter;

a plurality of slots extending from the clamping surface through to an oppositely facing back side;

a leaf spring coupled to the clamping surface for forcing the catheter into the depression and against the clamping surface;

a plurality of access holes in between the plurality of slots and extending from the back side through to the clamping surface and;

a plurality of push rods, where in each one of the plurality of push rods is disposed within each of the plurality of access holes to thereby lift the leaf spring from off the catheter when the catheter must be manipulated;

an actuable means for pushing the push rods through the plurality of access holes when catheter is to be manipulated; and means for feeding the catheter to the clamping device.

* * * * *